(12) United States Patent
Bert et al.

(10) Patent No.: US 8,405,050 B2
(45) Date of Patent: Mar. 26, 2013

(54) METHOD AND APPARATUS FOR IRRADIATION OF A MOVING TARGET VOLUME

(75) Inventors: Christoph Bert, Uttenreuth (DE); Gerhard Kraft, Darmstadt (DE); Eike Rietzel, Weiterstadt (DE); Alexander Gemmel, Mainz (DE)

(73) Assignee: GSI Helmholtzzentrum Fuer Schwerionenforschung GmbH, Darmstadt (DE)

( * ) Notice: Subject to any disclaimer, the term of this patent is extended or adjusted under 35 U.S.C. 154(b) by 176 days.

(21) Appl. No.: 12/678,562

(22) PCT Filed: Sep. 25, 2008

(86) PCT No.: PCT/EP2008/008169
§ 371 (c)(1),
(2), (4) Date: Jun. 24, 2010

(87) PCT Pub. No.: WO2009/040117
PCT Pub. Date: Apr. 2, 2009

(65) Prior Publication Data
US 2010/0301235 A1 Dec. 2, 2010

Related U.S. Application Data

(60) Provisional application No. 60/995,168, filed on Sep. 25, 2007.

(30) Foreign Application Priority Data

Sep. 25, 2007 (DE) .......................... 10 2007 045 879

(51) Int. Cl.
*G01J 1/00* (2006.01)
(52) U.S. Cl. ................ 250/491.1; 250/492.1; 250/492.3

(58) Field of Classification Search ................ 250/491.1
See application file for complete search history.

(56) References Cited

U.S. PATENT DOCUMENTS
(Continued)

FOREIGN PATENT DOCUMENTS
DE      10031074 A1    1/2002
DE    102004028035 A1   12/2005
(Continued)

OTHER PUBLICATIONS

Volume Conformal Irradiation of Moving Target Volumes with Scanned Ion Beams, Groezinger, S.O., Doctoral thesis,pp. 1-191, Darmstadt, 2004.*

(Continued)

*Primary Examiner* — Phillip A Johnston
(74) *Attorney, Agent, or Firm* — Leydig, Voit & Mayer, Ltd.

(57) ABSTRACT

A method of determining an actual, especially an actual effective, radiation dose distribution of a moving target volume includes detecting first and further positions of volume elements of the target volume in a first and at least one further motional state of the moving target volume, determining transformation parameters by transformation of the first positions into the further positions, irradiating the moving target volume in accordance with an irradiation plan which comprises a plurality of raster points to be irradiated, wherein during the irradiation of a raster point it is detected which of the motional states is occupied by the moving target volume, assigning raster points to subirradiation plans and determining the actual effective dose for each of the plurality of volume elements, in each case from contributions from the raster points of the subirradiation plans using the transformation parameters. Calculation and application of correction parameters which compensate for changes, caused by movement, to the position of the Bragg maximum and to the biologically effective dose applied.

14 Claims, 5 Drawing Sheets

U.S. PATENT DOCUMENTS

| | | |
|---|---|---|
| 6,661,870 B2 | 12/2003 | Kapatoes et al. |
| 7,197,404 B2 | 3/2007 | Holland |
| 7,482,606 B2 | 1/2009 | Groezinger et al. |
| 2003/0136924 A1 | 7/2003 | Kraft et al. |
| 2005/0143965 A1 | 6/2005 | Failla et al. |
| 2005/0201516 A1 | 9/2005 | Ruchala et al. |
| 2006/0033042 A1 | 2/2006 | Groezinger et al. |
| 2006/0074292 A1 | 4/2006 | Thomson et al. |
| 2006/0159324 A1 | 7/2006 | Ritt et al. |
| 2008/0071131 A1 | 3/2008 | Rietzel |
| 2009/0095921 A1 | 4/2009 | Bert et al. |

FOREIGN PATENT DOCUMENTS

| | | |
|---|---|---|
| DE | 102005063220 A1 | 6/2007 |
| DE | 102006044139 A1 | 3/2008 |
| WO | WO 2007079854 A2 | 7/2007 |

OTHER PUBLICATIONS

Groezinger, S.O., Volume Conformal Irradiation of Moving Target Volumes with Scanned Ion Beams, Doctoral thesis, pp. 1-191, Darmstadt, 2004.*

Bert, Bestrahlungsplanung für bewegte Zielvolumina in der Tumortherapie mit gescanntem Kohlenstoffstrahl Internet Citation, [Online] Feb. 3, 2006, XP002481370 Retrieved from the Internet: URL:http://elib.tu-darmstadt.de/diss/00064 8> [retrieved on Jun. 24, 2008], obtained from internet at http://tuprints.ulb.tudarmstadt.de/epda/000648/BERT_phd_belegexemplar_a.pdf on Sep. 16, 2010.

Bert et al., 4D treatment planning for scanned ion beams, Radiation Oncology, Biomed Central Ltd, LO, vol. 2, No. 1, Jul. 3, 2007, p. 24, XP021030775 ISSN: 1748-717X, obtained from internet at http://www.ro-journal.com/content/pdf/1748-717X-2-24.pdf on Sep. 16, 2010.

International Search Report for PCT/EP2008/008169 mailed on Dec. 2, 2009.

Kanai et al., Irradiation of mixed beam and design of spread-out Bragg peak for heavy-ion radiotherapy, Radiat Res 147:78-85, 1997.

Kramer et al., Rapid calculation of biological effects in ion radiotherapy, Phys Med Biol 51: 1959-1970, 2006.

Zaider et al., The synergistic effects of different radiations, Radiat Res 83:732-739, 1980.

* cited by examiner

METHOD AND APPARATUS FOR IRRADIATION OF A MOVING TARGET VOLUME

CROSS REFERENCE TO RELATED APPLICATIONS

The present application is the national stage of international application PCT/EP2008/008169, filed on Sep. 25, 2008, and claims the benefit of the filing date (German Application No. 10 2007 045 879.9, and U.S. provisional application Ser. No. 60/995,168, both filed on Sep. 25, 2007.

The present invention relates to a method and apparatus for determining an actual radiation dose distribution, to a method and apparatus for establishing an irradiation plan, to a method and apparatus for determining a radiation dose compensation and also to an apparatus for irradiation, each of which can be used in the context of irradiating moving target volumes.

Tumour therapy using particle beams, especially protons, α particles and carbon nuclei, is increasing in importance. In that context, the raster scanning method has a number of advantages compared with other methods. In the raster scanning method, a three-dimensional raster is placed over or across the tumour volume. The particle beam is deflected by deflecting magnets in two directions perpendicular to one another. By actively varying the particle energy, the position of the Bragg peak, in which the largest portion of the dose is deposited, is set at different tissue depths. Known scanning methods are, for example, spot scanning, continuous scanning and uniform scanning.

In particle therapy using a scanned particle beam, movements of the target area generally result in a deterioration of the planned dose distribution. When a movement of the target area is superimposed with the scanning movement this can result in doses that are to high, called overdoses in the context of the invention, and doses that are too low, called underdoses, in any part of the target area.

DE 100 31 074 A1 is related to irradiation by means of raster scanning methods in the static case.

DE 10 2004 028 035 A1 is related to a compensation of three-dimensional movements of a target volume during ion beam irradiation.

The dissertation "Bestrahlung für bewegte Zielvolumen in der Tumortherapie mit gescanntem Kohlenstoffstrahl"; C. Bert; Technische Universitat Darmstadt; 1 Feb. 2006 shows possibilities for a dose calculation in the presence of a movement and also possibilities for a calculation of compensation vectors and pre-irradiation corrections for movement-compensated irradiations.

The article "4D treatment planning for scanned ion beams"; Christoph Bert, Eike Rietzel; 3 Jul. 2007; http://www.ro-journal.com/content/2/1/24 addresses beam treatment of tumours that move as a result of respiratory movements of a patient.

DE 10 2005 063 220 A1 deals with a calculation of an absorbed radiation dose during the movement and the modification of the beam position taking into account the dose absorbed. In the case of the absorbed dose, it is assumed that the total dose is linear with respect to a particle number. Partial doses are calculated in each movement phase and subsequently accumulated in a reference state.

In the case of materials exhibiting non-linearity between the absorbed dose and the dose effect, that is to say the action, it is not the absorbed dose but rather the actual effective dose that is relevant.

In the case of biological samples, for example in the context of a patient irradiation, this is especially the actual biologically effective dose, in brief the biologically effective dose. On the other hand, in the case of a detector, for example a scintillator or a film, reference is made to, especially, effectiveness or efficiency of the material.

The actual dose describes the dose that is deposited in a material, be it tissue or some other material, for example detector material or film material, considering a movement (see below for determination). The actual dose corresponds to the total dose, that is deposited in a material taking into account the movement. The actual effective dose describes the effect of a deposited dose considering a movement. The effect can be dependent on the deposited dose—especially, also, in a non-linear manner (see below for determination).

It is an object of the present invention to provide a method and apparatus for determining an actual radiation dose distribution, a method and apparatus for establishing an irradiation plan, a method and apparatus for determining a radiation dose compensation and also an apparatus for irradiation, which are capable of considering movements of an irradiated target volume.

The present invention is based on the idea of calculating the actual radiation dose and compensation parameters in the course of the irradiation of a moving target volume with particle beams. As a result, despite the movement of the target volume, an actual radiation dose optimised for a stationary reference case can be deposited in the moving target volume. The actual radiation dose, especially the actual effective dose, can be, for example, an actual biologically effective dose or a material effectiveness or efficiency.

As particle beams, charged or uncharged particle beams can be employed. As charged particle beams there can be used, for example, protons, helium ions or carbon ions.

The biologically effective dose is formed by weighting the physical dose absorbed by the target volume, especially the actual dose, with a relative biological effectiveness. The absorbed dose deposited in a moving target volume and the compensation parameters can be calculated by the methods disclosed in DE 10 2005 063 220 A1.

A material effectiveness or efficiency of the dose is formed by weighting the physical dose absorbed by the target volume, especially the actual dose, with a relative efficiency (in the case of detectors this is also sometimes referred to as detector yield).

The actual effective dose can therefore refer, for example, to the actual biologically effective dose or also to the material effectiveness or efficiency. For brevity, reference is sometimes as well made to the effective dose. The relative biological effectiveness and the relative efficiency are subsumed herein under the more comprehensive term relative effectiveness.

In an advantageous manner, the approach according to the invention makes the calculation of the actual effective dose possible, especially the biologically effective dose or the material effectivness or efficiency, even during movement of the target volume. In this case, completely new irradiation systems are not required, because the approaches according to the invention can be put into practice as add-ons to existing irradiation systems. In addition, the approach according to the invention makes possible a compensated treatment of the moving target volume with the actual effective dose in the case of a scanned particle beam. This has the positive effect, for example in the case of a tumour treatment, that a minimal beam loading of the healthy tissue is achievable without loss of therapeutic action within the moving target volume.

A number of terms that are used in describing the present invention will be explained hereinbelow.

A "target volume" is a region or body to be irradiated by a particle beam. The target volume can consist of any material that is to be investigated, or that is treatable, by means of radiation. The target volume can especially consist of a material in which a linear relationship between the number of particles deposited and the dose effect (action) is not present (films, scintillators, biological tissue). The target volume can move during the irradiation. Such movements can be movements in any direction or also rotations. The movements can also result in changes concerning the shape of the target volume.

A "voxel", or "volume element", corresponds especially to a cubic subdivision of a volume data set typically having edge lengths of approximately $(1\times1\times2)$ mm$^3$. The volume data set includes parameters of the target volume to be irradiated. The volume data set can be, for example, a patient volume data set resulting from, for example, computed tomography or a dose calculation.

A "raster point", or "grid position" (x, y, E, N, F) is a 3D coordinate (x, y, E), in the scanner system coordinate system, of a Bragg maximum with a number of particles N to be applied at a beam focus F as part of an irradiation plan. The lateral coordinates x, y are orthogonal to the beam direction; the energy E describes the isoenergy layer, that is to say a layer having the same depth of the penetration in the beam direction. For the purpose of movement compensation, the location of the raster point can be modified during the course of the irradiation plan. This modification can be described by the parameters $\Delta x$, $\Delta y$, $\Delta E$, $\Delta N$ and also, possibly, $\Delta F$. In that context, for example in a first step in a transformation of one motional state into another motional state, only the spatial location of the coordinates x, y, E of a raster point is transformed. The location (x, y, E) of the Bragg maximum can also be described by a 3D coordinate within a volume data set. For example, a transformation of the raster point coordinates into a computed tomography (CT) coordinate system results in the spatial location of the raster point in the volume data set.

An "irradiation plan" is a set of raster points applied to a patient at one or more defined table and beam incident angles using a particular primary particle, for example $^{12}$C, p. For example, an irradiation plan can have 10$^4$ raster points. During movement, the order of raster point application plays a part because there is, for example, an interaction with a tumour movement.

It is possible to describe a movement of the target volume by means of a "movement trajectory" or a "movement substitute variable". For example, a 3D trajectory of a tumour can be tracked by implanted gold beads+fluoroscopy, that is to say X-ray video, or radio transponders. Alternatively or additionally thereto, a substitute variable can be measured, from the movement of which generally only the phase and/or motional state of, for example, the target area movement or, also, the phase or motional state of the surrounding anatomy, especially the anatomy in the entry region, becomes evident. This is sufficient for a four-dimensional computed tomography (4DCT) image and breathing-synchronised irradiation with correlation to the target area movement being present. As a substitute variable there can be used, for example, a movement of the abdominal wall, a respiratory flow or a respiration temperature.

A "movement phase" or a "motional state" is a portion of the movement of the target volume. The movement of the target volume can be divided into a plurality of movement phases or motional states. One of the movement phases or motional states is frequently defined as reference. For example, a movement phase can define a portion of the cyclic breathing period by means of the phase or amplitude of the movement trajectory. In this context, a movement phase corresponds to a temporal portion of a 4DCT, that is to say a phase of the 4DCT. Accordingly there exists a temporal correlation between the movement phase and the corresponding 4DCT phase.

A "mixed field" is understood to be the particle and energy spectrum at a particular location/voxel of the irradiated area. The particle and energy spectrum provides information relating to the amount and energy of the various particles at that location and is, because of the fragmentation of the primary beam, dependent on the latter's initial energy and the depth of the location. The biological effectiveness of a particular mixed field can be described by "alpha" and "beta" values, which, in accordance with the linear quadratic model, allow the absorbed dose D to be converted, by calculation, into a survival value S (see, for example, Kanai T et al, 1997, Irradiation of mixed beam and design of spread-out Bragg peak for heavy-ion radiotherapy, Radiat Res 147:78-85, and Zaider M, Rossi HH, 1980, The synergistic effects of different radiations, Radiat Res 83:732-739): $S=\exp(-\text{alpha}*D+\text{beta}*D*D)$. For the invention, the alpha and beta values can be determined especially in accordance with Kramer M, Scholz M, 2006, Rapid calculation of biological effects in ion radiotherapy, Phys Med Biol 51: 1959-1970. In the case of detectors, the efficiency establishes the relationship between absorbed dose and detector signal and can, depending on the detector and model, be described by one or more parameters.

In accordance with one embodiment, the present invention provides a method of determining an actual radiation dose distribution, especially an actual effective radiation dose distribution, in the case of irradiation of a moving target volume which has a plurality of volume elements, having the following steps:

detecting first positions of the plurality of volume elements in a first motional state of the moving target volume;

detecting further positions of the plurality of volume elements in at least one further motional state of the moving target volume;

determining transformation parameters by means of transformation of the first positions into the further positions;

irradiating the moving target volume in accordance with an irradiation plan having a plurality of raster points to be irradiated, wherein during the irradiation of a raster point it is detected which of the motional states is occupied by the moving target volume;

assigning raster points, during the irradiation of which the moving target volume occupied the first motional state, to a first sub-irradiation plan;

assigning raster points, during the irradiation of which the moving target volume occupied the at least one further motional state, to at least one further sub-irradiation plan; and determining the actual dose for at least one of the plurality of volume elements, in each case from contributions from the raster points of the first sub-irradiation plan and of the at least one further sub-irradiation plan, using the transformation parameters.

The method can, of course, be used in the course of an actual irradiation, but also in principle in the course of a simulated irradiation, for example as a preliminary to an actual irradiation. The actual and/or actual effective radiation dose distribution can also be determined in a simulation. It is possible to obtain information therefrom as to how to proceed with a subsequent irradiation. Where appropriate, it is possible to determine a modification of the irradiation plan in order to modify an irradiation for a desired actual and/or actual effective dose distribution.

Some or even the majority of the volume elements of the target volumes therein do not necessarily need to be only those volume elements which actually correspond to a raster point. The volume elements can also include other volume elements that are important for an irradiation such as, for example, those volume elements that surround the volume elements to be irradiated such as, for example, tissue that is to be spared or volume elements located in an entry channel.

The transformation parameters can be determined, for example, by registering the first motional state relative to the further motional state. This means, for example, that in a 4DCT that phase which corresponds to the first motional state is registered relative to that phase which corresponds to the further motional state. In this context, the registration can be a rigid registration or also a non-rigid registration. Which registration is used herein will depend on the computing outlay and on the desired accuracy.

Transformations between two movement phases can, for example, be determined/optimised iteratively. The basis is the 4DCT data set, that is to say one 3D CT per movement phase. The transformation specification is optimised until a comparison measure describing the concordance of two CT cubes after the transformation becomes minimal. Typical comparison measures are the sum of the squared differences of the voxel values/grey values or the NMI (normalised mutual information), a measure of entropy. There are several known/published approaches for possible transformation specifications.

A sub-irradiation plan herein is that part of an irradiation plan which is assigned to a particular motional state. For example, those raster points which are irradiated during a motional state are part of the sub-irradiation plan assigned to that motional state. The raster points of the sub-irradiation plan can especially also be modified for the assigned motional state. For example, an irradiation plan can be defined in a first motional state, that is to say the reference motional state. Then, if raster points are irradiated during another motional state—if those raster points are therefore applied to the sub-irradiation plan—the coordinates of those raster points, for example x, y and E, can be transformed by applying to the coordinates of those raster points that transformation which transforms the reference motional state into the further motional state. As a result, there is obtained a modification of the raster points in line with that motional state during which the raster points are being applied.

In summary, it can be said, in other words, that all the motional states occurring during the irradiation can be taken into account for determination of the actual dose and in each case the absorbed dose is calculated in order to be subsequently summed taking into account the required transformation. The parameters for calculation of the actual effective dose can then (see hereinbelow) be summed taking into account the corresponding transformation in each case in order to calculate the effect of the radiation dose inclusive of all parameters.

In accordance with a further embodiment, the present invention provides a method of establishing an irradiation plan having correction values for irradiation of a moving target volume which has a plurality of volume elements, having the following steps:

detecting first positions of the plurality of volume elements in a first motional state of the moving target volume;

detecting further positions of the plurality of volume elements in at least one further motional state of the moving target volume;

determining transformation parameters by means of transformation of the first positions into the further positions;

establishing an irradiation plan for the irradiation of the moving target volume on the basis of the first positions, the irradiation plan having a plurality of raster points to be irradiated;

determining correction parameters for each raster point and motional state on the basis of the transformation parameters, the correction parameters allowing modification of the irradiation plan in line with the at least one further motional state, and the correction parameters being storable in a storage area of a computer unit;

determining first contributions from a raster point which are suitable for use in the calculation of an actual, especially actual effective, radiation dose of raster points to be irradiated subsequently in the first motional state;

determining, taking into account the correction parameters, second contributions from a raster point which are suitable for use in the calculation of an actual, especially actual effective, radiation dose of raster points to be irradiated subsequently in the at least one further motional state; and forming correction contributions, especially difference contributions, from the first and second contributions, the correction contributions being storable in a storage area of a computer unit.

The determined correction parameters can be archived, especially for subsequent use, in a memory of a computer unit, for example in a correction table held there. In analogous manner, the determined correction contributions can be archived in a memory of a computer unit, for example in the same table as the correction parameters or in a further correction table.

In addition to or together with the correction contributions, further information can also possibly be stored, for example in a joint table. Such information can relate, for example, to particle spectra and can be used in a more far-reaching calculation of the actual effective dose.

In accordance with a further embodiment, the present invention provides a method of determining a radiation dose compensation in the case of irradiation of a moving target volume, having the following steps:

providing an irradiation plan having correction parameters and correction contributions in accordance with a method of the present invention;

determining a current motional state and a current raster point during irradiation of the moving target volume in accordance with the irradiation plan;

reading out a current correction parameter from its storage area, the current correction parameter being assigned to the current motional state and the current raster point;

determining, using the correction contributions, an actual radiation dose already applied to the current raster point on account of previously irradiated raster points; and modifying the radiation dose provided for the current raster point in accordance with the irradiation plan, taking into account the current correction parameter and the actual radiation dose already applied.

The invention will be explained in greater detail hereinbelow by way of example with reference to the accompanying Figures, in which.

In order to counter the disruptive influence of movement of the target volume during irradiation, the beam location and the beam intensity can be modified in line with the particular current position of the target volume. For the purpose, the lateral beam position, the reach in the depth direction and also, where appropriate, the particle number can be modified in line with the course of the movement of the target volume. Especially when modifying the particle number it is necessary to take into account the relevant actual effective dose. When the target volume is, for example, a tumour, the particle number should be established taking into account the biologically effective dose relevant to the patient; when the target volume is, for example, detector material, the particle number should be established taking into account the relative efficiency relevant to the material.

The biologically effective dose can be obtained from the absorbed dose by multiplication with the relative biological effectiveness. The relative biological effectiveness is dependent not only on particle number but also on particle species and particle energy, the nature of the target tissue and the applied, absorbed dose. The calculation of the relative biological effectiveness usually includes the cell survival, which is dependent on the parameters mentioned. The material effectiveness can be correspondingly obtained from the absorbed dose by taking into account the relative efficiency. The relative efficiency too is dependent not only on particle number but also on particle species and particle energy, the nature of the target material and the applied, absorbed dose. The calculation of the material effectiveness usually includes the effect, which is dependent on the parameters mentioned. It is also possible in this case first to determine the action and, using that, to calculate the relative efficiency.

In general, the relative biological effectiveness varies from location to location. At a particular location in the target volume, the relative biological effectiveness is determined by the absorbed dose, the particle spectrum and energy spectrum and the type of material that is hit. In respect of the particle spectrum it is the case that, for particles which are heavier than protons, the primary beam will fragment on interaction with material and/or tissue, giving rise to lighter particles such as, for example, H, He or Li. The type of material that is hit can be, for example, tumour tissue, for example of the lungs or skin.

In accordance with the present invention, for calculation of the biologically effective dose the relative biological effectiveness can be taken into account fully with all its dependencies—this of course also applying correspondingly to the material effectiveness with the corresponding relative efficiency. In order to calculate the biologically effective dose at a point of the reference motional state, the anatomical position of that point is first transformed into each other motional state of the target volume. In that manner, for the reference state in dependence on the course of the irradiation, the parameters that determine the relative biological effectiveness can be generated by transfer from the other states. This is possible for each anatomical position of the reference state. First, there is determined the particle and energy spectrum resulting from all the partial beams that are applied in the individual motional states. This is summed to form an overall spectrum for particle species and particle energy. Then, from the overall spectra there is calculated the resulting biologically effective dose, the relative biological effectiveness and/or the cell survival—or, in corresponding manner, the resulting material effectiveness and relative efficiency.

In order to modify the particle number in line with the movement of the target volume, a control system can determine the particle number corrections necessary for achieving a desired dose. This can be accomplished on the basis of the calculated particle and energy spectra. In accordance with one example of an embodiment, requisite correction parameters can be pre-calculated and made available to the control system, for example in the form of a table. Accordingly, the control system can, during tracking of the course of the irradiation, determine with the aid of the correction parameters whether, and where appropriate how, the particle number is to be modified in line with the current irradiation point in order to achieve the desired dose.

Figure 1:
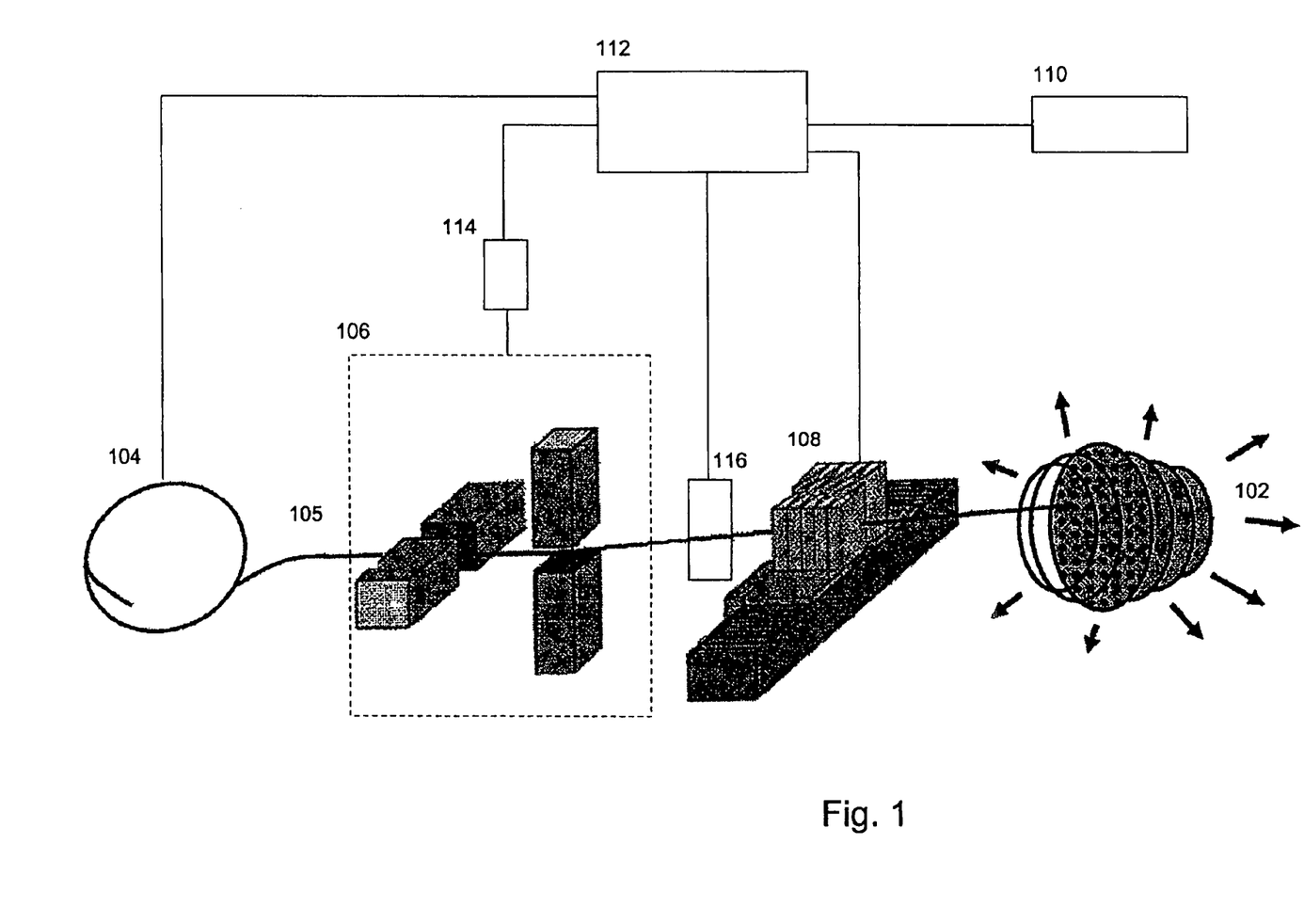
FIG. 1 shows, in diagrammatic form, an irradiation system.

FIG. 1 shows, in diagrammatic form, an irradiation system. The irradiation system can comprise the apparatuses according to the examples of embodiments of the present invention and can be arranged to carry out the methods according to the examples of embodiments of the present invention.

In accordance with this example of an embodiment, the irradiation system is arranged to irradiate a target volume 102. The target volume 102 can be a moving target volume. This is indicated in FIG. 1 by means of arrows surrounding the target volume 102. Further indicated are individual layers of the target volume 102. An isoenergy layer of the target volume is irradiated with a particular energy of particle beam, for example a $^{12}C$ beam. The target volume 102 can be, for example, a tumour.

The irradiation system has a synchrotron or any other accelerator 104 for delivering a particle beam 105. Lateral deflection of the particle beam 105, as is already required for the irradiation of stationary target volumes (raster scanning method), and lateral compensation of the movement of the target volume can be accomplished by means of scanning magnets 106. The scanning magnets 106 can be, for example, dipole magnets, in which case the lateral compensation can be accomplished by modifying the dipole magnet settings. For longitudinal compensation along the beam axis, the irradiation system has an energy variation device. For example, the energy variation device has the form of a wedge system 108 for passive energy modulation. The wedge system 108 can have, for example, wedges made of plastics material which can be moved by means of a linear motor. The invention described herein can be used for any type of energy variation device, and can also, for example, be arranged for an active energy variation by an appropriately equipped accelerator. The irradiation can be carried out in accordance with an irradiation scheme having a plurality of raster points.

The irradiation system can furthermore have a detecting device 110, a control device 112, a raster scan unit 114, and a particle counter 116. The detecting device 110 can be arranged, for example, to detect a movement of the target volume 102, and make the detected movement available to the control device 112. The particle counter 116 can be arranged to provide the control device 112 with the number of particles in the particle beam 105. The particle counter 116 can be an ionisation chamber. The control device 112 can be arranged to control the accelerator 104, the scanning magnets 106 and the energy modulation system 108. For that purpose the control device 112 can be arranged to determine corresponding control parameters from the data received from the detection device 110 and the particle counter 116.

Figure 2:
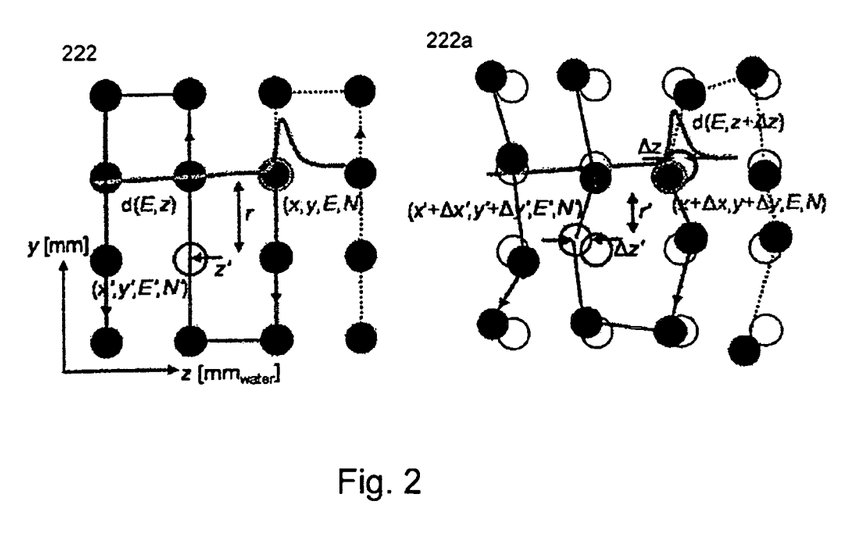
FIG. 2 shows, in diagrammatic form, raster points of an irradiation scheme.

FIG. 2 shows, in diagrammatic form, raster points which are arranged on a grid in accordance with an irradiation scheme. In accordance with that irradiation scheme, the raster points are irradiated in temporal succession as indicated by the arrows. If the target volume assumes different motional states, the positions of the raster points change. The left-hand diagram of FIG. 2 shows the raster points in a reference motional state of the target volume. By way of example, one of the reference points is provided with a reference numeral 222. The right-hand diagram of FIG. 2 shows the raster points in a further motional state of the target volume. By way of example, a point 222 in the further motional state is provided with a reference numeral 222a.

In case of the reference motional state shown in the left-hand diagram, the dose contributions from each grid position (x, y, E, N) to subsequently irradiated grid positions (x', y', E', N') can be calculated. The calculation is based on the lateral distance r and the depth z'.

In case of the further motional state shown in the right-hand diagram, changes in the actual effective dose contribution $\Delta D$ are calculated. The calculation is based on the current 4DCT phase and includes adaptation of the position of the Bragg maximum $\Delta(x, y, z)$ and $\Delta(x', y', z')$. This results in a displacement of the depth-dose distribution $d(E, z+\Delta z)$, a displacement from z' by $\Delta z'$, and a change in the lateral distance (r').

Figure 3:
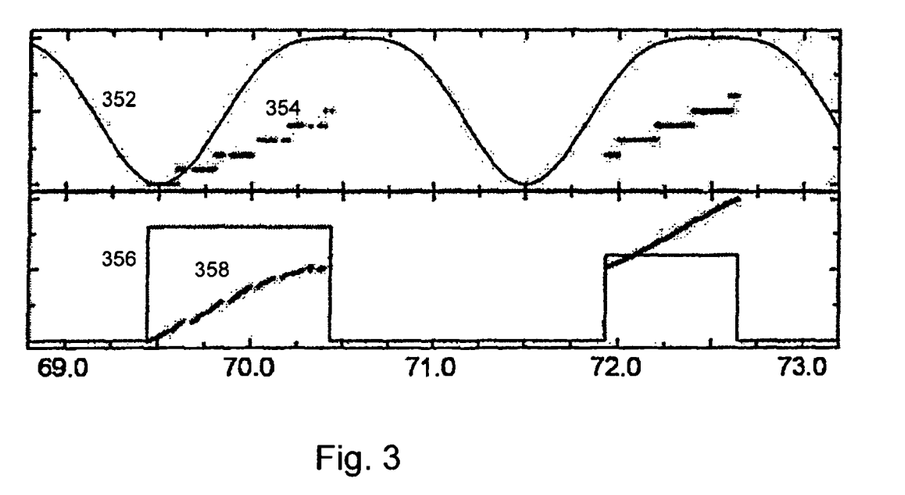
FIG. 3 shows a temporal correlation of a scanning process with a movement of the target volume.

FIG. 3 shows a temporal correlation of a scanning process with a movement of the target volume. This correlation can be used for calculation of the requisite actual effective radiation dose in case the scanning process is simulated or for calculation of the applied radiation dose after an irradiation has been performed.

The upper graph refers to the movement or motion of the target volume. On the vertical axis there are plotted the motional states of the target volume as the absolute position 352 and as the movement phase 354. On the horizontal axis there is plotted the time in seconds. On the basis of a movement trajectory 352, the current motional state 354 of the target volume can be determined. In this example of an embodiment, ten motional states have been used. The trajectory 352 shows the movement of the target volume. The trace 354 shows the associated motional states of the target volume.

The lower graph refers to the accelerator of the irradiation system. On the vertical axis there are plotted the grid positions 358, which correspond to the raster points, and the beam intensity 356. On the horizontal axis there is plotted the time in seconds. The course of scanning is determined by the extracted radiation intensity 356 and the number of particles per grid position N. The course of scanning, that is to say, the delivery time for each and every grid position, is not linear because N is generally not the same for different raster points. The trace 356 shows the intensity of the particle beam. The trace 358 shows the irradiated grid position.

Figure 4:
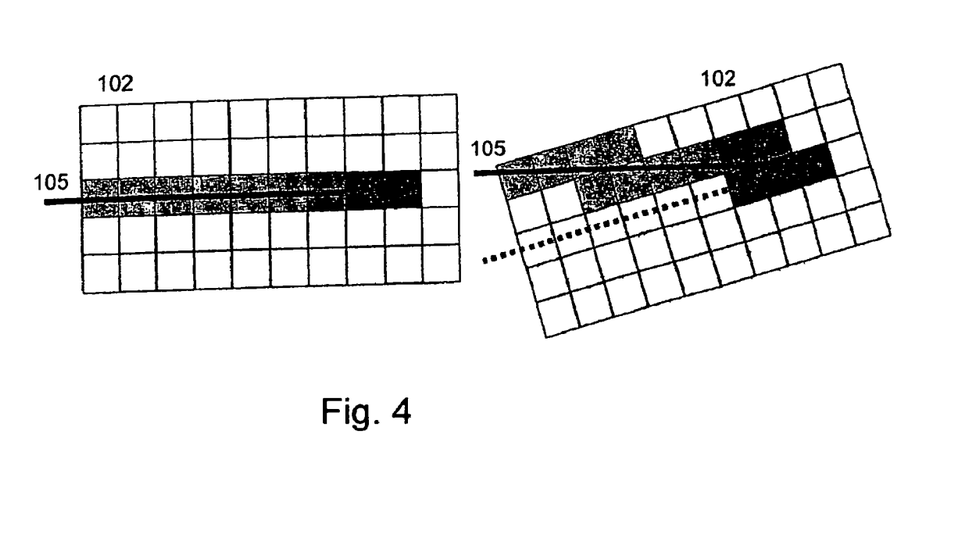
FIG. 4 shows, in diagrammatic form, two motional states of the target volume.

FIG. 4 shows, by way of example, in schematical diagram, two motional states of the target volume 102. The target volume has a plurality of voxels, each of which is shown in FIG. 4 by a small square. The left-hand diagram shows the target volume in a first motional state, which serves as reference. The particle beam 105 penetrates into the target volume to the point of the target volume. The irradiation affects not only the target voxel but also the voxels located in the entry channel of the particle beam 105. Those voxels located in the entry channel are already subjected to pre-irradiation as a result of the irradiation of the target voxel. Depending on the motional state of the target volume, different voxels are affected by the pre-irradiation. The influence of a rotation of the target volume on the pre-irradiation is shown in the right-hand diagram. As a result of the rotation of the target volume, the dose in the entry channel of the particle beam 105 changes in comparison to the reference case shown on the left. A comparable effect occurs in the case of deformations and generally non-rigid movements of the target area.

Figure 5:
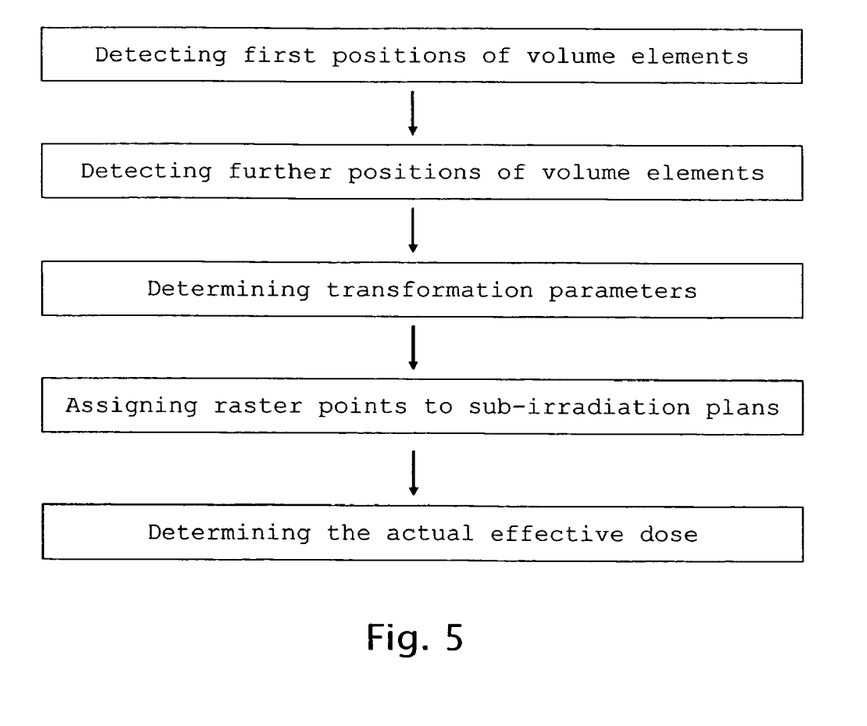
FIG. 5 shows a flow diagram of a method of determining an actual effective radiation dose distribution.

FIG. 5 shows a flow diagram of a method of determining an actual effective radiation dose distribution in the case of irradiation of a moving target volume, in accordance with an example of an embodiment of the present invention. The moving target volume can be the target volume 102 shown in FIG. 1. As shown in FIG. 4, the target volume has a plurality of volume elements. In accordance with this example of an embodiment, the target volume can assume a first and a second motional state as shown in FIG. 4. The first motional state is defined as the reference motional state.

Firstly, in accordance with the method, there are detected those positions of the volume elements which are occupied by the volume elements when the moving target volume 102 occupies the first motional state. In corresponding manner, there are detected those positions of the volume elements which are occupied by the volume elements when the moving target volume 102 occupies the second motional state. If more than two motional states are defined for the moving target volume 102, this method step and the subsequent method steps are also carried out in corresponding manner for the further motional states.

After detection of the positions, the first positions are transformed into the second positions in order to determine transformation parameters. The transformation can be carried out in accordance with a predetermined transformation specification. For example, the determination of the transformation parameters can be carried out by means of registration of the motional states.

The moving target volume 102 is irradiated in accordance with an irradiation plan. The irradiation plan has a plurality of raster points 222 to be irradiated. The irradiation plan will have been established on the basis of the reference motional state, that is to say in accordance with the set of first positions. In order to take account of the motion or movement of the target volume 102, various irradiation techniques can be employed. In the case of the interrupted radiation technique, there is carried out an interruption in the course of the irradiation that is modified in line with the movement of the target volume (gating). Alternatively, the irradiation technique can include application of the irradiation plan more than once (rescanning) or a movement compensation by means of compensation parameters. With an appropriate arrangement of the irradiation plan, the irradiation can also be carried out without a special irradiation technique that is to say as for stationary target volumes.

During the irradiation procedure, for each individual raster point irradiated it is possible to detect which of the motional states is currently occupied by the moving target volume 102. Alternatively, the detection can also be carried out for a group of irradiated raster points in each case.

The detection of the particular motional states makes it possible for irradiated raster points to be assigned to the particular motional states. Accordingly, raster points 222, during the irradiation of which the moving target volume 102 actually occupied the first motional state, can be assigned to a first sub-irradiation plan. Correspondingly, raster points 222a, during the irradiation of which the moving target volume 102 actually occupied the further, second motional state, can be assigned to a second sub-irradiation plan. Insofar as the moving target volume 102 can assume still further motional states, further sub-irradiation plans can be established in corresponding manner.

On the basis of the established sub-irradiation plans, the actual effective dose can be determined. In particular, the actual effective dose can be determined for each volume element in each case using contributions from the raster points 222, 222a of the first sub-irradiation plan and the second sub-irradiation plan. The determination can be carried out using the transformation parameters. Accordingly, the contributions from the raster points 222a of the further sub-irradiation plan can be determined by a transformation of the first positions into the second positions.

When, for example, the actual effective dose actually deposited in one of the volume elements is to be calculated, the particle and energy spectrum present during the irradiation of the raster point 222 can, for example, contribute thereto. The contribution is generally a different contribution when the raster point 222 has been irradiated during a first motional state, that is to say as part of the first sub-irradiation plan, compared to the case when the raster point 222a has been irradiated during a second motional state. By virtue of the method, the actual effective dose can now also be calculated in dependence on the various motional states.

The contributions from the raster points 222, 222a used to determine the actual effective dose can in each case include parameters for calculation of an absorbed radiation dose and a relative effectiveness, especially a relative biological effectiveness or also a relative efficiency. The relative effectiveness can be influenced by the radiation dose absorbed by the volume element, the particle energy of the irradiation, the particle spectrum of the irradiation and/or the material type of the volume element. The parameters can be determined together with detection of the positions of the volume elements.

The method according to this example of an embodiment can be carried out, for example, by the irradiation system shown in FIG. 1.

For the purpose, by way of example, the detecting device 110 of the irradiation system can have a device for detecting first positions of the plurality of volume elements in a first motional state and a device for detecting further positions of the plurality of volume elements in at least one further motional state of the moving target volume 102. Furthermore the detecting device 110 can be arranged to detect, during the irradiation of a raster point, which of the motional states is currently occupied by the moving target volume 102.

The control device 112 of the irradiation system can have, for example, a device for determining transformation parameters by means of transformation of the first positions into the further positions and a device for assigning raster points to the assigned motional states in order to establish sub-irradiation plans. The control device 112 can furthermore have a device for the determination of the actual effective dose from contributions from the raster points 222, 222a of the sub-irradiation plans.

In accordance with a further example of an embodiment, a method of calculating the actual biologically effective dose distribution during movement or motion of the target volume includes the following steps:

In a first step, a recording is made of temporally resolved volume data sets from which a 3D movement or motion of the target volume, for example a tumour, and the surrounding anatomy is apparent and which are suitable for calculating the particle reach. Taking into account the movement of the anatomy is important especially in the beam path. For recording the volume data sets, it is possible to use 4DCTs, with the CTs subdividing a cycle of the movement or motion of the tumour, for example a breathing cycle, into 10 quasi-stationary 3DCTs, 4DCT phases. One of the 4DCT phases is defined as the reference phase. For the example of the breathing cycle, the 4DCT phase on breathing out is typically used as the reference phase.

Contouring of the tumour volume and, where appropriate, of the organs at risk, is carried out at least in the reference motion or movement phase but also, where appropriate, in the remaining 4DCT phases.

There follows the determination of the transformation specification, by means of which, for example, a transfer of all voxel centre-points of the selected reference phase into the other, in this case for example nine, 4DCT phases can be accomplished. For the purpose there are used non-rigid registration methods with the associated transformation algorithms and, for example, a comparison metric such as, for example, correlation metrics, normalised mutual information or the sum of squared differences.

An optimisation of a quasi-static reference irradiation plan is carried out on the basis of the reference phase and the corresponding contours. The application and dose calculation of that reference irradiation plan results in a static reference dose distribution in the coordinate system of the reference phase. For example, an actual effective dose distribution, especially a biologically effective dose or a material effectiveness, can be optimised.

There follows an irradiation of a patient using the reference irradiation plan. The irradiation can be carried out without any change to the reference irradiation plan, for example resulting from interruption of the course of irradiation (gating), application of the irradiation plan more than once (rescanning) or with movement compensation by application of compensation parameters ($\Delta x$, $\Delta y$, $\Delta E$, $\Delta N$, $\Delta F$). In all cases, the patient geometry changes during the irradiation as a result of organ movement. Modelling of the organ movement can be carried out, for example prior to the irradiation, by means of 4DCT. In a preferred embodiment, it can be checked immediately prior to irradiation, by means of suitable methods (where appropriate fluoroscopy) whether the modelling is still valid.

During the irradiation there is carried out time-resolved measurement of the particle extraction from the synchrotron. Alternatively, and in generally equivalent manner, a measurement of the irradiation timepoint of each raster point can be carried out. In addition, a measurement of the movement trajectory of the tumour or of a suitable substitute variable is carried out. In that context it is necessary for all the measurements to be time-correlated.

There follows an assignment of the raster point to the movement phase and as a result to the 4DCT. As a result, for each movement phase there is formed a sub-irradiation plan. On application to the assigned 4DCT phase there arises a sub-dose distribution, which can be transformed into the reference movement phase with the aid of the transformation specifications. The sub-dose distribution comprises only the absorbed, physical dose. In the reference movement phase, summing of all the dose distributions is carried out to form a total absorbed, physical dose. For the actual effective dose, however, sub-dose distributions cannot as yet be calculated in that manner because the relative effectiveness, especially the relative biological effectiveness or the relative efficiency, is influenced by the parameters of the other sub-irradiation plans.

A calculation of the actual effective dose, especially the biologically effective dose or the material effectiveness, during movement is now carried out by calculation in the reference coordinate system. In order to determine the dose of a voxel, the contribution from all raster points of all sub-irradiation plans is calculated to form an overall particle and energy spectrum. For the purpose, the voxel central point is transformed into the coordinate system of the corresponding movement phase and, taking into account the 4DCT phase that is applicable therein, the parameters for calculation of absorbed dose, especially a lateral spacing relative to the voxel and a water-equivalent depth, and the relative activity, especially a particle and energy spectrum, are collected. From the totality of parameters for each voxel there can be calculated the relative activity and the absorbed dose and, as a result, the actual effective dose, especially the biologically effective dose or the material effectiveness (see above in regard of the determination of the actual effective dose and of the relative activity by way of the action).

The methods described with reference to FIG. 5 are suitable for the calculation of the actual effective dose distribution, especially the biological effectiveness and the material effectiveness, during movement of the target volume and can be applied to various techniques for minimising the influence of movement.

Figure 6:
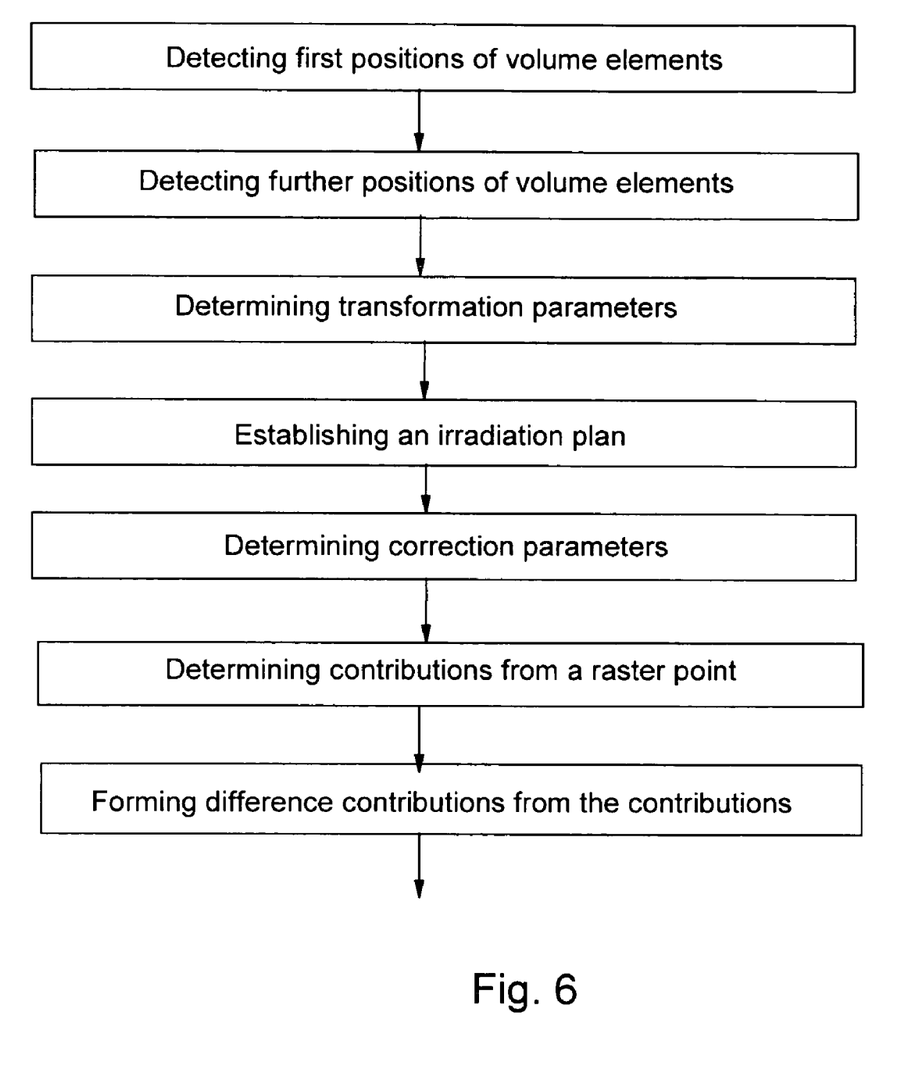
FIG. 6 shows a flow diagram of a method of determining a radiation dose compensation.

FIG. 6 shows a flow diagram of a method of establishing an irradiation plan with correction values, which is suitable for the irradiation of a moving target volume, in accordance with an example of an embodiment of the present invention. The moving target volume can again be the target volume 102 shown in FIG. 1, which has, as shown in FIG. 4, a plurality of volume elements and which can assume a first and second motional state, the first motional state being defined as the reference motional state.

Firstly, as already described with reference to FIG. 5, in the first method steps first and further positions of the plurality of volume elements in the first or second motional state of the moving target volume 102 are detected. Subsequently, as a result of transformation of the first positions into the further positions, transformation parameters are determined.

In a next step, an irradiation plan for irradiation of the moving target volume 102 can be established. The irradiation plan is established on the basis of the first positions and again has a plurality of raster points 222 to be irradiated.

On the basis of the transformation parameters there can now be determined correction parameters for each raster point and motional state. The correction parameters make it possible for the irradiation plan to be modified in line with the further motional state. Such a modification is necessary, because the positions of the volume elements can differ in the different motional states. The correction parameters can be stored, for example, in a correction table.

For each raster point 222 of the first motional state there can be determined first contributions which can be used for the calculation of an actual radiation dose of raster points to be irradiated subsequently. Subsequent raster points in this context are raster points which are irradiated in the first motional state after, in terms of time, that raster point 222 for which the first contributions are being determined at that very time.

In corresponding manner, there can be determined, for each raster point 222a of the second motional state, second contributions which can be used for calculation of an actual effective radiation dose of raster points to be irradiated subsequently. Subsequent raster points in this context are raster points which are irradiated in the further motional state after, in terms of time, that raster point 222a for which the second contributions are being determined at that very time. If the moving target volume can assume further motional states, further contributions for the corresponding raster points can be determined in that manner for those further states in corresponding manner.

After the determination of the first and second contributions, there can be formed therefrom a correction contribution, in particular a difference contribution. The correction contribution can also be stored in a correction table; that table can, but need not, be the same as the correction table for the correction parameters.

In accordance with this example of an embodiment, the raster points determine in each case a position of a Bragg maximum in the first motional state. A correction parameter which is assigned to a raster point defines a change to the position of the Bragg maximum in the second motional state. By way of example, the correction parameters can define a lateral and longitudinal change to the Bragg maximum.

The method according to this example of an embodiment can be carried out, for example, by the irradiation system shown in FIG. 1.

For that purpose, the detecting device 110 of the irradiation system can have a device for detecting first positions of the plurality of volume elements in a first motional state and a device for detecting second positions of the plurality of volume elements in at least one further motional state of the moving target volume 102.

The control device 112 of the irradiation system can have, for example, a device for determining transformation parameters by means of transformation of the first positions into the second positions and a device for establishing an irradiation plan for irradiation of the moving target volume 102. The control device 112 can furthermore have a device for determining correction parameters for each raster point and motional state, a device for storing the correction parameters, for example in a first correction table, a device for determining first contributions from a raster point 222, a device for determining second contributions from a raster point 222a, a device for forming correction contributions, especially difference contributions, from the first and second contributions, and a device for storing the correction contributions, for example in a second correction table.

In accordance with a further example of an embodiment, a method of calculating compensation parameters for motion or movement-compensated irradiation includes the following steps.

In a first step, as described with reference to FIG. 5, there are firstly established 4DCT, transformation parameters and a reference irradiation plan.

There follows a calculation of the parameters $\Delta x$, $\Delta y$, $\Delta E$ and, where appropriate, $\Delta F$ for each raster point and movement phase and storage of the parameters, for example in a first correction table. Known methods can be used for the calculation.

Known methods can likewise be used for the determination of the absorbed dose.

For the reference movement phase, there are carried out determination and storage of the contributions from a raster point which are required for calculation of the actual effective dose for all raster-points-in-the-CT which are subsequently irradiated.

For all further movement phases there is carried out the same calculation as for the reference movement phase, although on 4DCT and taking into account the $\Delta x$, $\Delta y$, $\Delta E$ and, where appropriate, $\Delta F$ of the raster points and raster-points-in-the-CT.

There follows a formation of correction contributions, especially difference contributions, from the parameters and storage, for example in a further correction table which can, but need not, correspond to the correction table having the correction parameters.

The methods described with reference to FIG. 6 make it possible to establish an irradiation plan on the basis of correction parameters and correction contributions, optionally saved in correction tables, the application of which includes a correction for movement and in the process takes into account the biologically effective dose.

Figure 7:
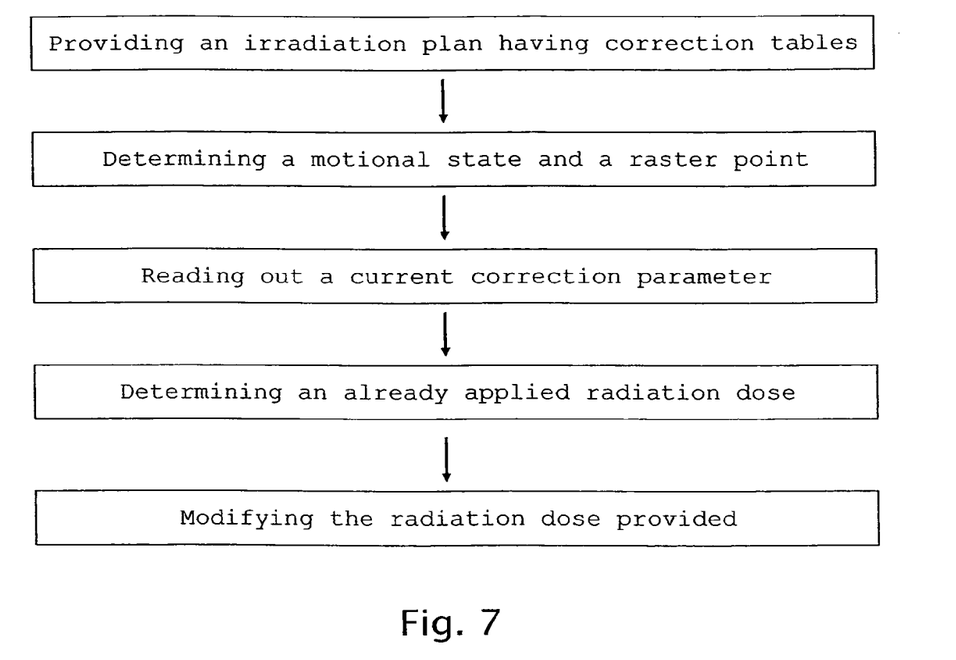
FIG. 7 shows a flow diagram of a method of determining a radiation dose compensation.

FIG. 7 shows a flow diagram of a method of determining a radiation dose compensation in the case of the irradiation of a moving target volume, in accordance with an example of an embodiment of the present invention. The moving target volume can again be the target volume 102 shown in FIG. 1.

In a first method step, there is carried out provision of an irradiation plan, of correction parameters, optionally in a first correction table, and of correction contributions, optionally in a second correction table. The irradiation plan and the correction parameters and correction contributions can be established by means of the methods described with reference to FIG. 6.

During an irradiation of the moving target volume 102 in accordance with the irradiation plan, a current motional state of the target volume 102 is detected. For the purpose, a raster point 222 currently to be irradiated in accordance with the irradiation plan is detected.

The current motional state and the current raster point are used to read out, for example from the first correction table, a current correction parameter, which is assigned to the current motional state and the current raster point.

By virtue of an irradiation of preceding raster points, a radiation dose will already have been applied to the current raster point, as shown with reference to FIG. 4. Using the correction contributions, for example from the second correction table, this radiation dose already applied to the current raster point can be determined.

In order to irradiate the current raster point with the radiation dose provided according to the irradiation plan, the radiation dose provided for the current raster point can be modified. This modification can be carried out on the basis of the current correction parameter and the radiation dose already applied.

The modification step can be carried out by comparing the radiation dose provided according to the irradiation plan with the radiation dose already applied. In accordance with the obtained result of the comparison, the particle number provided for irradiation of the current raster point can be modified. By way of example, the particle number can be reduced in order to take into account irradiation resulting from preceding raster points.

For determining the radiation dose already applied, deviation amounts can be logged for each raster point 222. For that purpose, the irradiation is detected which has already been applied to the current raster point by virtue of previously irradiated raster points. The deviation amounts can be used for calculating a particle number difference, which can be used to modify the particle number to be applied in accordance with the irradiation plan.

The method according to this example of an embodiment can be carried out, for example, by the irradiation system shown in FIG. 1.

For the purpose, the detecting device 110 of the irradiation system can further have, in addition to the devices already described with reference to FIG. 6, a device for determining a current motional state and a current raster point 222 during an irradiation of the moving target volume 102 in accordance with the irradiation plan. The control device 112 can further have a device for reading out a current correction parameter, for example from the first correction table, a device for determining a radiation dose already applied to the current raster point and a device for modification of the radiation dose.

In accordance with a further example of an embodiment, a method of applying the compensation parameters during irradiation includes the following steps.

In a first step, as the basis, correction parameters and correction contributions and also the reference irradiation plan are established as described with reference to FIG. 6. Also, the movement detection for the determination of the movement phase, which is required for access to the look-up table, is carried out, and the raster point currently being irradiated, which is also required for access to the look-up table, is detected.

The values $\Delta x$, $\Delta y$, $\Delta E$ are determined and can be read out from an optionally established first correction table; they can be parameterised by the current movement phase and the current raster point.

A modification of the particle number is carried out in dependence on whether as a result of the irradiation of all previous raster points a greater or lesser actual effective dose than intended in the reference plan was applied. The particle number is increased or reduced accordingly. In the process, $\Delta D$ can be read out from an optionally established correction table. For the purpose, there is carried out, in the irradiation of prior raster points by application of the correction contributions, a logging and, as a result of corresponding counters, a taking into account of the deviation amounts in the case of raster points irradiated later, taking into account the actual effective dose. Immediately prior to the irradiation of a raster point, the corresponding counter is evaluated and there is carried out a calculation of $\Delta N$ on the basis of the deviation amounts summed in the counter and of N and/or of the dose of the reference irradiation plan. Both steps can be carried out on-line. They cannot be pre-calculated because the sequence of movement phase to raster point cannot be planned, because it is influenced by the movement trajectory and the scanning process and consequently is generally different in each treatment.

The calculation of the correction parameters for modification of the particle number is dealt with in greater detail hereinbelow; two approaches are presented. The raster points are consecutively numbered in the order of their irradiation from 1 to M.

Approach 1 ("On-Line Survival"):

Prior to irradiation, at each raster point and each phase of movement or motion (called movement or motional phase), alpha, beta and other dose weights, that is to say parameters that are required for the calculation of the actual effective dose, are pre-calculated for all raster points to be irradiated beforehand and are saved in a control unit. When multiplied by the particle number of the associated raster point, these weights give the contributions from the raster point to the parameters that are important for the calculation of survival, alpha, beta and absorbed dose of the mixed field. At the start of the irradiation, a list is drawn up in which the particle number introduced and the movement or motional phase applicable at that timepoint are noted for each raster point. Before the irradiation of a point, the particle number from the list is multiplied by the weight belonging to the corresponding movement or motional phase and accumulated for all predecessor points. From this there can be determined on-line alpha, beta and the absorbed dose of the mixed field and consequently the previously applied actual effective dose. From the difference relative to the desired value of the actual effective dose, the particle number of the current point is so determined that the actual effective dose corresponds to that desired. The corrections and also, consequently, the pre-calculations do not necessarily have to be limited to the raster point positions but can also be related to volume elements and/or other locations.

The accumulation of the individual contributions (weight multiplied by particle number) can also be carried out for each point immediately after the irradiation of a point and/or in the extraction pause, for which it would then be necessary to have a further on-line list with one entry per point.

Approach 2 ("Spectrum Method"):

Before the irradiation, energy and particle spectra normalised to each raster point and to each movement or motional phase are pre-calculated with a suitable energy binning for all raster points to be irradiated subsequently and are made available in a table to a control unit. This means that, at the first raster point to be irradiated, normalised spectra are calculated for each movement phase for the raster points 2 to M; at the second raster point, spectra are calculated for each movement phase for the raster points 3 to M, etc. In the process, depending on the distance from the current raster point, it is also possible to dispense with the calculation and storage for the further raster points if there is no contribution or a negligible contribution.

Furthermore, the desired spectra, as resulting from the reference plan, are created at the start of the irradiation for all points (except the first), in which subsequently on-line the difference from the actual contribution of a point is to be stored. During the irradiation of a point, the movement or motional phase is measured and for all subsequent points the normalised spectra of the current movement phase are multiplied by the difference between the introduced and the planned particle number for the current point and added to the spectra created initially. Before irradiation of the next point, from the energy and particle spectra calculated on-line in that manner there is determined the previously applied actual effective dose and the particle number of the current point is correspondingly modified so that overall the desired actual effective dose is obtained. For this purpose, the dE/dx table of the biological target/detector material and the intrinsic efficiency and/or RBA/RBE tables are also necessary. The corrections and also, consequently, the pre-calculations do not necessarily have to be limited to the raster point positions but can also be related to volume elements and/or other reference locations.

An apparatus which is arranged to carry out the methods described with reference to FIG. 7 can contain the correction parameters and correction contributions optionally in correction tables and is arranged to carry out the logging of the parameters for the calculation of $\Delta N$ and to calculate, before the irradiation of a raster point, the $\Delta N$ necessary for a biologically effective dose compensation.

The above-described steps of the methods according to the invention can be carried out in a plurality of separate methods and at different points in time. Also, individual method steps can be carried out in parallel with one another or also, if appropriate, in a different order. In addition, the methods and apparatuses described by way of example can be combined with one another.

Features that are disclosed in the context of one of the methods can also be of relevance to one of the apparatuses and vice-versa.

The described examples of embodiments can be generally applied in systems for the irradiation of material, especially if the material moves or is moved relative to the reference system of the equipment and if the effect to be obtained in the material is non-linearly dependent on the absorbed dose.

List of Reference Numerals 102 target volumes
104 accelerator
105 particle beam
106 scanning magnet
108 wedge system
110 detecting device
112 control device
114 raster scan unit
116 particle counter
222 reference point
222a reference point
352 movement or motion of target volumes
354 motional states
356 beam intensity
358 grid position production time

The invention claimed is:

1. A method of determining an actual effective radiation dose distribution in the case of irradiation of a moving target volume which has a plurality of volume elements, having the following steps:
   detecting first positions of the plurality of volume elements in a first motional state of the moving target volume;
   detecting further positions of the plurality of volume elements in at least one further motional state of the moving target volume;
   determining transformation parameters by means of transformation of the first positions into the further positions;
   irradiating the moving target volume in accordance with an irradiation plan having a plurality of raster points to be irradiated, wherein during the irradiation of a raster point it is detected which of the motional states is occupied by the moving target volume;
   assigning raster points, during the irradiation of which the moving target volume occupied the first motional state, to a first sub-irradiation plan;
   assigning raster points, during the irradiation of which the moving target volume occupied the at least one further motional state, to at least one further sub-irradiation plan; and
   determining the actual effective dose for at least one of the plurality of volume elements, in each case from contributions from the raster points of the first sub-irradiation plan and of the at least one further sub-irradiation plan, using the transformation parameters, each of the contributions from the raster points of the first sub-irradiation plan and of the at least one further sub-irradiation plan including parameters for calculation of an absorbed radiation dose and a relative effectiveness.

2. The method recited in claim 1, wherein the step of determining the actual dose includes transformation of the first positions into the further positions so as to determine the contribution from the raster points of the at least one farther sub-irradiation plan.

3. The method recited claim 1, wherein the relative effectiveness in a volume element is influenced by at least one of the radiation dose absorbed by the volume element, a particle and energy spectrum of the irradiation and a material type of the volume element.

4. The method recited in claim 1, wherein the irradiating includes establishing the irradiation plan on the basis of the first positions.

5. The method recited in claim 1, wherein the irradiating includes interrupting a course of the irradiation, applying the irradiation plan more than once or providing a movement or motional compensation using compensation parameters, so as to account for movements of the moving target volume.

6. An apparatus for determining an actual radiation dose distribution during irradiation of a moving target volume having a plurality of volume elements, the apparatus comprising:
   a device for detecting first positions of the plurality of volume elements in a first motional state of the moving target volume;

a device for detecting further positions of the plurality of volume elements in at least one further motional state of the moving target volume;

a device for determining transformation parameters by means of transformation of the first positions into the further positions;

a device for irradiating the moving target volume in accordance with an irradiation plan having a plurality of raster points to be irradiated, wherein the irradiating device is further arranged to detect, during the irradiation of a raster point, which of the motional states is occupied by the moving target volume;

a device for assigning raster points, during the irradiation of which the moving target volume occupies the first motional state, to a first sub-irradiation plan;

a device for assigning raster points, during the irradiation of which the moving target volume occupies the at least one further motional state, to at least one further sub-irradiation plan; and a device for determining the actual dose for at least one of the plurality of volume elements, in each case from contributions from the raster points of the first sub-irradiation plan and of the at least one further sub-irradiation plan, using the transformation parameters, each of the contributions from the raster points of the first sub-irradiation plan and of the at least one further sub-irradiation plan including parameters for calculation of an absorbed radiation dose and a relative effectiveness.

7. A method for establishing an irradiation plan having correction values for irradiation of a moving target volume with a plurality of volume elements, the method comprising:

detecting first positions of the plurality of volume elements in a first motional state of the moving target volume;

detecting further positions of the plurality of volume elements in at least one further motional state of the moving target volume;

determining transformation parameters by means of transformation of the first positions into the further positions;

establishing an irradiation plan for the irradiation of the moving target volume on the basis of the first positions, the irradiation plan having a plurality of raster points to be irradiated;

determining correction parameters for each raster point and motional state on the basis of the transformation parameters, the correction parameters allowing modification of the irradiation plan in line with the at least one further motional state, and the correction parameters being storable in a storage area of a computer unit;

determining first contributions from a raster point which are suitable for use in the calculation of an actual radiation dose of raster points to be irradiated subsequently in the first motional state;

determining, taking into account the correction parameters, second contributions from a raster point which are suitable for use in the calculation of an actual radiation dose of raster points to be irradiated subsequently in the at least one further motional state, the first and second contributions including parameters for calculation of an absorbed radiation dose and a relative effectiveness; and establishing correction contributions from the first and second contributions, the correction contributions being storable in a storage area of a computer unit.

8. The method recited in claim 7, wherein a raster point defines a position of a Bragg maximum in the first motional state and an assigned correction parameter defines a change to the position of the Bragg maximum in the at least one further motional state.

9. Method according to claim 8, wherein the correction parameter assigned to a respective raster point defines a lateral and longitudinal change to the Bragg maximum.

10. A system comprising an apparatus for establishing an irradiation plan having correction values for irradiation of a moving target volume which has a plurality of volume elements, the apparatus including:

a device for detecting first positions of the plurality of volume elements in a first motional state of the moving target volume;

a device for detecting further positions of the plurality of volume elements in at least one further motional state of the moving target volume;

a device for determining transformation parameters by means of transformation of the first positions into the further positions;

a device for establishing an irradiation plan for the irradiation of the moving target volume on the basis of the first positions, the irradiation plan having a plurality of raster points to be irradiated;

a device for determining correction parameters for each raster point and motional state on the basis of the transformation parameters, the correction parameters allowing modification of the irradiation plan in line with the at least one further motional state, and the correction parameters being storable in a storage area of a computer unit;

a device for determining first contributions from a raster point which are suitable for use in the calculation of an actual radiation dose of raster points to be irradiated subsequently in the first motional state;

a device for determining, taking into account the correction parameters, second contributions from a raster point which are suitable for use in the calculation of an actual radiation dose of raster points to be irradiated subsequently in the at least one further motional state, the first and second contributions including parameters for calculation of an absorbed radiation dose and a relative effectiveness; and a device for forming correction contributions from the first and second contributions, the correction contributions being storable in a storage area of a computer unit.

11. A method of determining a radiation dose compensation for irradiation of a moving target volume, the method comprising:

detecting first positions of the plurality of volume elements in a first motional state of the moving target volume;

detecting further positions of the plurality of volume elements in at least one further motional state of the moving target volume;

determining transformation parameters by means of transformation of the first positions into the further positions;

establishing an irradiation plan for the irradiation of the moving target volume on the basis of the first positions, the irradiation plan having a plurality of raster points to be irradiated;

determining correction parameters for each raster point and motional state on the basis of the transformation parameters, the correction parameters allowing modification of the irradiation plan in line with the at least one further motional state, and the correction parameters being storable in a storage area of a computer unit;

determining first contributions from a raster point which are suitable for use the calculation of an actual radiation dose of raster points to be irradiated subsequently in the first motional state;

determining, taking into account the correction parameters, second contributions from a raster point which are suitable for use in the calculation of an actual radiation dose of raster points to be irradiated subsequently in the at least one further motional state, the first and second contributions including parameters for calculation of an absorbed radiation dose and a relative effectiveness;

establishing correction contributions from the first and second contributions, the correction contributions being storable in a storage area of a computer unit;

determining a current motional state and a current raster point during irradiation of the moving target volume in accordance with the irradiation plan;

reading out a current correction parameter from its storage area, the current correction parameter being assigned to the current motional state and the current raster point;

determining, using the correction contributions, a radiation dose already applied to the current raster point on account of previously irradiated raster points; and modifying the radiation dose provided for the current raster point in accordance with the irradiation plan, taking into account the current correction parameter and the radiation dose already applied.

12. The method recited in claim 11, wherein the modifying, includes comparing the radiation dose provided in accordance with the irradiation plan with the radiation dose already applied and wherein a particle number provided for irradiation of the current raster point is modifiable in accordance with a result of the comparison.

13. The method recited in 11, wherein the determining a radiation dose already applied includes logging deviation amounts for each raster point due to irradiation of previous raster points and further includes calculating, before irradiating the current raster point, a particle number difference on the basis of the deviation amounts and the particle number to be applied in accordance with the irradiation plan.

14. The system recited in claim 10, further comprising an apparatus for determining a radiation dose compensation in the case of irradiation of a moving target volume, the apparatus including a device for determining a current motional state and a current raster point during irradiation of the moving target volume in accordance with the irradiation plan; and a device for reading out a current correction parameter, the current correction parameter being assigned to the current motional state and the current raster point;

a device for determining, using the correction contributions, a radiation dose already applied to the current raster point on account of previously irradiated raster points; and a device for modifying the radiation dose provided for the current raster point in accordance with the irradiation plan, taking into account the current correction parameter and the radiation dose already applied.

* * * * *

UNITED STATES PATENT AND TRADEMARK OFFICE
CERTIFICATE OF CORRECTION

PATENT NO.       : 8,405,050 B2
APPLICATION NO.  : 12/678562
DATED            : March 26, 2013
INVENTOR(S)      : Christoph Bert et al.

Page 1 of 1

It is certified that error appears in the above-identified patent and that said Letters Patent is hereby corrected as shown below:

In the Claims:

Col. 18, line 46, claim 2,

--… at least one farther…-- should read "… at least one further…"

Col. 20, line 65, claim 11,

--… for use the calculation…-- should read "… for use in the calculation…"

Signed and Sealed this
Sixteenth Day of July, 2013

Teresa Stanek Rea
*Acting Director of the United States Patent and Trademark Office*